(12) United States Patent
Sakagami et al.

(10) Patent No.: US 7,519,427 B2
(45) Date of Patent: Apr. 14, 2009

(54) LOW FREQUENCY MEDICAL DEVICE, METHOD THEREFOR, PROGRAM AND RECORDING MEDIUM

(75) Inventors: Toshimasa Sakagami, Tokyo (JP); Hirotsugu Sato, Sagamihara (JP); Takashi Nemoto, Tokyo (JP)

(73) Assignees: ITO Co., Ltd., Tokyo (JP); Hirose Electric Co., Ltd., Kanagawa-Ken (JP)

( * ) Notice: Subject to any disclaimer, the term of this patent is extended or adjusted under 35 U.S.C. 154(b) by 490 days.

(21) Appl. No.: 10/844,164

(22) Filed: May 12, 2004

(65) Prior Publication Data
US 2004/0230253 A1    Nov. 18, 2004

(30) Foreign Application Priority Data
May 14, 2003   (JP)   ............... P 2003-136081

(51) Int. Cl.
*A61N 1/32* (2006.01)
(52) U.S. Cl. .......................... 607/43; 607/48
(58) Field of Classification Search ............ 607/16, 607/5, 29, 2, 43, 46, 59, 63
See application file for complete search history.

(56) References Cited

U.S. PATENT DOCUMENTS 4,922,906 A * 5/1990 Takeuchi et al. .............. 607/72
6,334,069 B1 * 12/2001 George et al. ................. 607/2
2001/0034541 A1 * 10/2001 Lyden .......................... 607/29
2002/0035383 A1 * 3/2002 Thompson .................... 607/16

FOREIGN PATENT DOCUMENTS

| JP | 10-179768   | 7/1998  |
|----|-------------|---------|
| JP | 2002-113115 | 4/2002  |
| JP | 2002-345979 | 12/2002 |
| JP | 2003-10145  | 1/2003  |

* cited by examiner

*Primary Examiner*—Carl H Layno
*Assistant Examiner*—Brian T Gedeon
(74) *Attorney, Agent, or Firm*—K & L Gates LLP

(57) ABSTRACT

Quantity and time for medical operation are measured after starting the medical operation (step S1). Parameters in a parameter protection mode and parameters in a standard mode are compared so as to determine whether or not contents in the parameters coincide and whether or not five minutes passes (step S2). If five minutes do not pass, it is detected whether or not a power supply switch is turned off (step S4). If it is not turned off, the operation returns to the step S1 so as to determine whether or not the power supply is turned off within five minutes in steps S3 and S4 while measuring the quantity and the time for the medical operation. If five minutes passes without turning off the power supply, data for the quantity and the time for the medical operation are loaded in a memory (step S5). After that, the operation is completed.

11 Claims, 4 Drawing Sheets

LOW FREQUENCY MEDICAL DEVICE, METHOD THEREFOR, PROGRAM AND RECORDING MEDIUM

The present application is based on patent application No. 2003-136081 filed May 14, 2003 in Japan, the content of which is incorporated herein by reference.

BACKGROUND OF THE INVENTION

1. Field of the Invention

The present invention relates to a low frequency medical device for performing a medical operation so as to stimulate muscles and nerves by applying a low frequency pulse to a human body, a method therefor, a device, a program which is used in the method, and a recording medium for recording the program.

2. Description of Related Art

Conventionally, a low frequency medical device has been known for purposes such as diet therapy, strengthening muscles, or curing pain or tension on an arm, a waist in human bodies by contracting muscles to which several electrodes are disposed so as to apply a low frequency electric current (see Japanese Unexamined Patent Applications No. 2003-10145 and No. 2002-345979)

In a case of such a low frequency medical device, an operator of a medical operation such as a doctor or a physical therapist consults with a user (patient) so as to determine necessary parameters for medical operations according to the use's condition and set the parameters in a medical device. For such parameters, it is possible to name a frequency for a low frequency pulse, a pulse width, and a time for the medical operation. The user bring back home a low frequency medical device in which the parameters are set so as to perform the medical operations at home. When the user activate the device under condition that electrodes of the device are disposed at predetermined positions on the user's body, the device is operated under a medical operation mode in which the predetermined parameters are effective.

After the predetermined medical operations are completed, the user visits the physical therapist or the doctor again. The physical therapist or the doctor asks predetermined questions to the user so as to evaluate the result for the medical operation according to the answers from the user. Consequently, the physical therapist or the doctor sets the parameters for the next medical operations according to the necessity.

Also, in a conventional low frequency medical device, a pulse generating circuit for generating a low frequency pulse is used according to a switching regulator method. FIG. 5A is a circuit diagram for showing an important portion of a conventional pulse generating circuit.

In FIG. 5A, for example, 10 kHz of a switching pulse is inputted into an input terminal 50 via a resistance R1 so as to switch a transistor Q1. Energy is stored in an inductance L from a power supply Vpp when the transistor Q1 is turned off. The stored electric energy is charged in a condenser C via a diode D when the transistor Q1 is turned off. The voltage in the condenser C increases in the above manner, Polarity of the increases output is switched in a circuit which is disposed in a rear stage such that a low frequency pulse can be obtained which has nearly 1 to 100 Hz of a bipolar rectangular waveform as shown in FIG. 5B.

However, in several cases in a conventional low frequency medical device, there have been problems below when the user responds to the questions by the physical therapist or the doctor. For example, the patient reports to the physical therapist or the doctor that the patient performed a medical operation at home even though the patient did not perform a medical operation actually. Also, the patient reports to the physical therapist or the doctor that the patient performed the medical operation at home according to the parameters which are set by physical therapist or the doctor even though the patient did not perform the medical operation according to the parameters which are different from the parameters which are determined by the physical therapist or the doctor. In other cases, the patient reports to the physical therapist or the doctor that the patient performed the medical operation at home according to the quantity and the time for the medical operation which are set by physical therapist or the doctor even though the patient did not perform the medical operation according to the above quantity and the time for the medical operation which are different from those which are determined by the physical therapist or the doctor.

Also, in a conventional pulse generating circuit according to a switching regulator method which is shown in FIG. 5A, there has been a problem in that it is not possible to obtain an output for increasing voltage which is not greater than the power supply voltage (for example, 12V). In a low frequency medical device, it is required that 1 to 45 V of output voltage must be adjusted by every 1 (one) V such that the output voltage should begin with 1V so as to avoid applying a high voltage to a human body instantly. It is not possible to obtain a voltage which is not greater than the power supply voltage Vpp in a circuit which is shown in FIG. 5A; thus, there has been a problem in that it is not possible to satisfy the above requirement.

SUMMARY OF THE INVENTION

The present invention is made for solving the above problem. An object of the present invention is to provide a low frequency medical device in which it is possible to acknowledge the quantity of the medical operation and the time for the medical operation accurately.

Another object of the present invention is to provide a low frequency medical device in which it is possible to start with the output voltage with 1V.

In order to solve the above problem, a low frequency medical device in a present invention for performing a medical operation by applying a low frequency pulse voltage to predetermined sections of a human body via electrodes comprises a measuring device for measuring a quantity and/or a time for the medical operation by outputting the low frequency pulse, a timer device for measuring a predetermined time with reference to a start of the medical operation, a detecting device for detecting a shut-down of a power supply, and a storage device for storing a time and/or a quantity for the medical operation which are measured by the measuring device after the predetermined time passes under condition that the power supply is not shut down such that the medical operation is performed by using parameters which are set by an physical therapist or the doctor.

Also, a low frequency medical device in the present invention for performing a medical operation by applying a low frequency pulse voltage to predetermined sections of a human body via electrodes comprises a pulse generating device for generating a low frequency pulse according to a switching regulator method, and a shut down device for a power supply which is supplied to the pulse generating device during a turned-off period of a switching element which forms the pulse generating device.

A method for a low frequency medical operation in the present invention by applying a low frequency pulse voltage to predetermined sections of a human body via electrodes comprises the steps for measuring a quantity and/or a time for the medical operation by outputting the low frequency pulse;

measuring a predetermined time with reference to a start of the medical operation, detecting a shut-down of a power supply, and storing a time and/or a quantity for the medical operation which are measured by the measuring device after the predetermined time passes under condition that the power supply is not shut down such that the medical operation is performed by using parameters which are set by an physical therapist or the doctor.

A computer program in the present invention for performing a medical operation by applying a low frequency pulse voltage to predetermined sections of a human body via electrodes comprises the steps for for measuring a quantity and/or a time for the medical operation by outputting the low frequency pulse, measuring a predetermined time with reference to a start of the medical operation, detecting a shut-down of a power supply, and storing a time and/or a quantity for the medical operation which are measured by the measuring device after the predetermined time passes under condition that the power supply is not shut down such that the medical operation is performed by using parameters which are set by an physical therapist or the doctor.

Also, the computer program according to Claim 13 is recorded in a recording medium of the present invention.

Operations

Therefore, in the present invention, the measured quantity of the medical operation and/or the time for the medical operations are stored when a predetermined period of time passes under condition that a power supply is not turned off during the medical operation. Therefore, it is possible to know the quantity of the medical operation and the time for the medical operation in the low frequency medical operation accurately and display the quantity of the medical operation and the time for the medical operation.

Also, in the present invention, an electricity does not flow in a condenser from a power supply because a power supply is turned off while the switching element is turned off. Therefore, it is possible to se the voltage in the condenser at the power supply voltage or lower.

As explained above, the quantity of the medical operation and the time for the medical operation are stored when a predetermined period of time passes after starting the medical operation. Therefore, by displaying the quantity of the medical operation and the time for the medical operation, the physical therapist or the doctor can realize the quantity of the medical operation and the time for the medical operation which is performed by the low frequency medical device which is used by the user accurately so as to set the parameters in the next medical operation.

Also, according to the present invention, another switching element which performs a synchronous operation with an ON/OFF operations in a switching regulator is disposed so as to shut down the power supply voltage during the switching element is turned off. Therefore, it is possible to set the output voltage at the power supply voltage or lower.

DETAILED DESCRIPTION OF THE INVENTION

Embodiments of the present invention are explained below with reference to attached drawings.

Figure 1A:
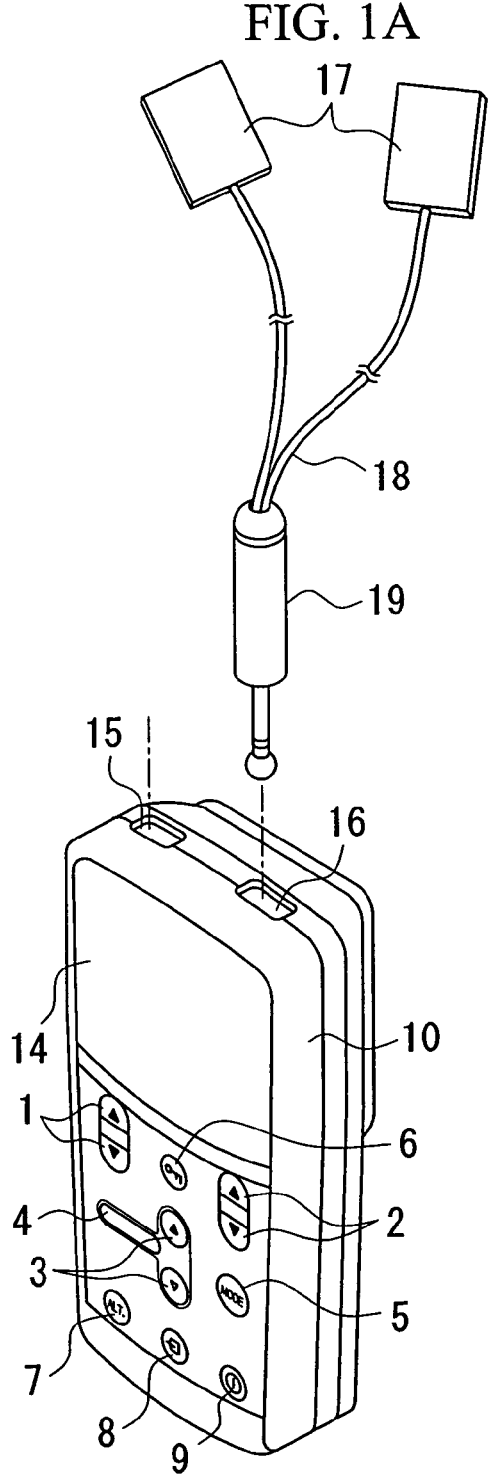
FIG. 1A is an external view of the low frequency medical device according to a first embodiment of the present invention
Figure 1B:
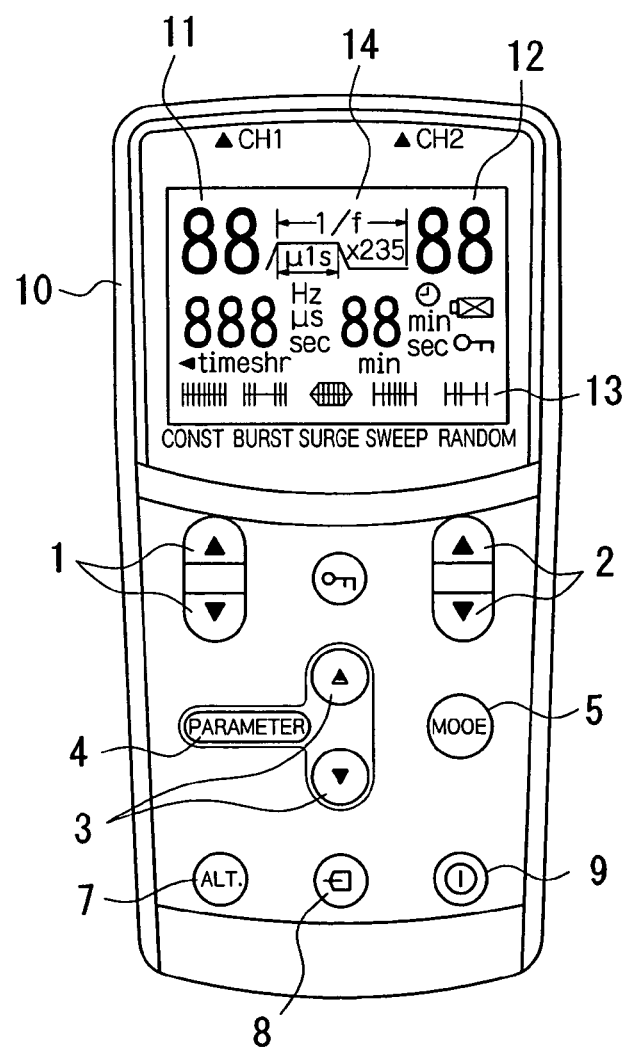
FIG. 1B is a front view therefor.

FIG. 1A is an external view of the low frequency medical device according to a first embodiment of the present invention. FIG. 1B is a front view therefore The low frequency medical device according to the present embodiment outputs two channels such as CH1 and CH2 of the low frequency pulse.

In FIGS. 1A and 1B, low frequency pulse outputting terminals 15, 16 are disposed on an upper surface of a casing 10. Plugs 19 to which a pair of electrodes 17 are connected via a lead wire 18 are connectable to the low frequency pulse outputting terminals 15, 16 respectively such that it is possible to perform the medical operation in both channels simultaneously. Various switches 1 to 9 which are formed by twelve push buttons and a liquid crystal display section 14 are disposed on a side surface of the casing 10. Switches 1 to 9 are as follows. Reference numeral SW1 indicates a CH1 up-down switch. Reference numeral SW2 indicates a CH2 output up-down switch Reference numeral SW3 indicates a parameter setting up-down switch. Reference numeral SW4 indicates a parameter selecting switch. Reference numeral SW5 indicates an output mode selecting switch. Reference numeral SW6 indicates a key-lock switch. Reference numeral SW7 indicates an alternating switch. Reference numeral SW8 indicates a switch for displaying quantity and time for the medical operation. Reference numeral SW9 indicates a power supply switch.

A CH1 output display section 11, a CH2 output display section 12, and an output mode display section 13 are disposed in a liquid crystal display section 14. Necessary data such as an output (level), a frequency, a pulse width, quantity of the medical operation, a time for the medical operation, etc. are displayed in a numeral form in the CH1 output display section 11 and CH2 output display section 12. A selected output mode is displayed in the output mode display section 13.

For such an output mode, it is possible to name modes which indicate five output patterns such as a CONST mode in which a pulse which has a constant output and frequency is outputted, a BURST mode in which a pulse which has a constant output and frequency is outputted for a certain period periodically, a SURGE mode in which a pulse which has a constant output and frequency is outputted gradually increasing manner and gradually decreasing manner, a SWEEP mode in which a frequency is swept at a constant output so as to be outputted, and a RANDOM mode in which the frequency which has a constant output is altered randomly so as to be outputted. When one of the output modes is selected, a symbol mark which indicates the selected output mode is displayed in the output mode display section 13.

Figure 2:
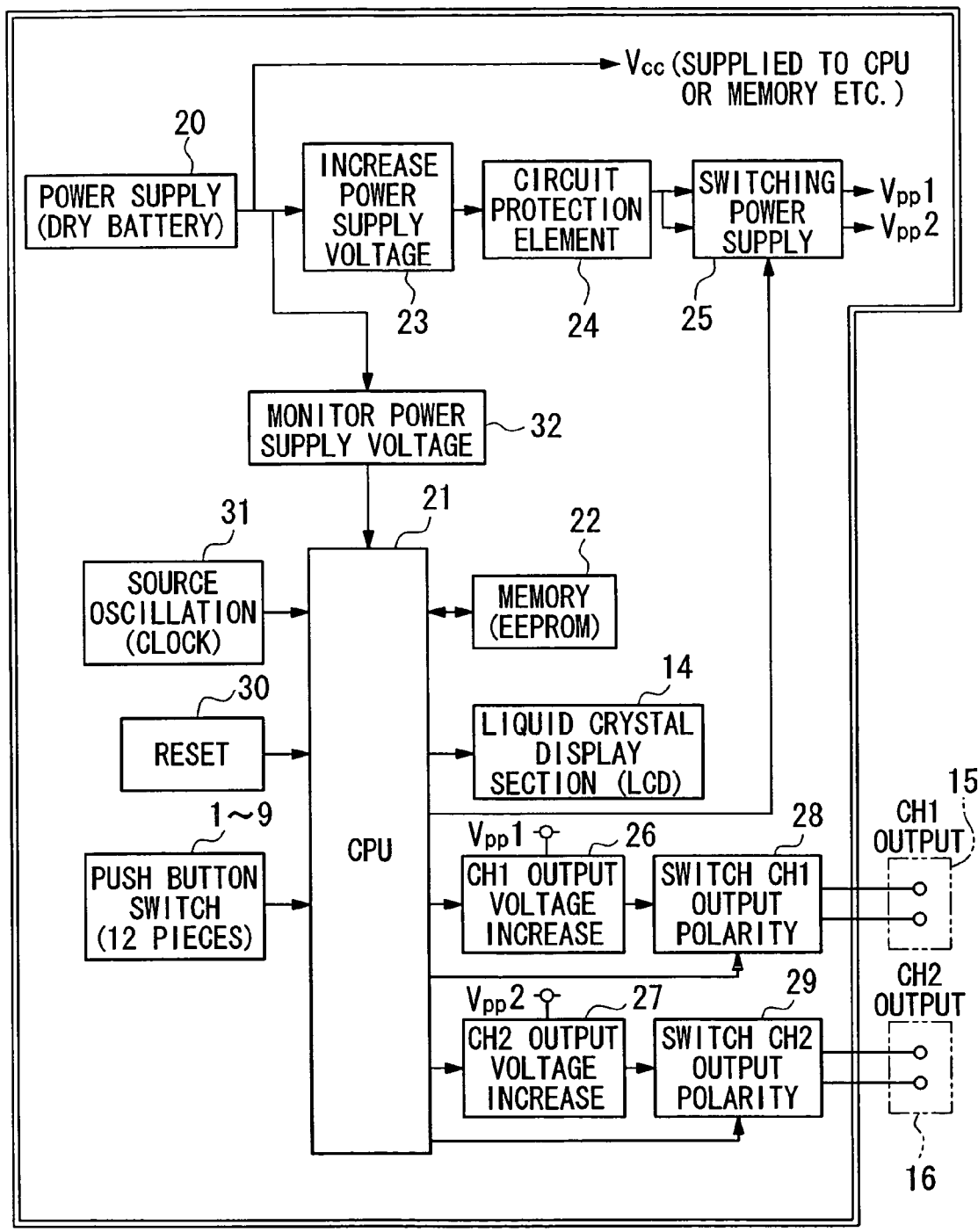
FIG. 2 is an electric block diagram for the low frequency medical device.

FIG. 2 is an electric block diagram for the low frequency medical device.

Figure 5A:
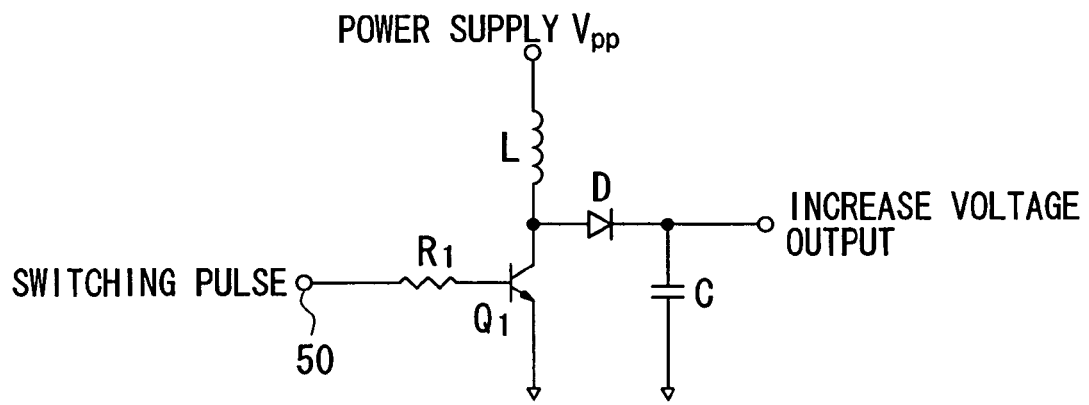
FIGS. 5A and 5B are circuit diagrams of a pulse generating circuit which is used in a conventional low frequency medical device.
Figure 5B:
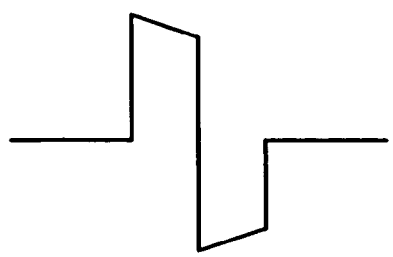

In FIG. 2, a power supply voltage Vcc which is outputted from a power supply 20 which is formed by a dry cell is supplied to necessary circuits such as a CPU 21, a memory 22, etc. Also, the power supply voltage Vcc is enhanced in the a power supply voltage enhancing section 23. After the voltage Vcc is protected in a circuit protection element 24, the voltage Vcc is switched in a power supply switching section 25 which is controlled by the CPU 21 so as to form two channels of voltage Vpp1 and Vpp2. The two channels of voltage Vpp1 and Vpp2 are supplied to a CH1 output voltage enhancing section 26 and a CH2 output voltage enhancing section 27 respectively which are controlled by the CPU 21. Polarity of the voltage which is enhanced in the CH1 output voltage enhancing section 26 is switched in a CH1 output polarity switching section 28 so as to form a low frequency pulse which is shown in FIG. 5B. Consequently, voltage which is enhanced in the CH1 output voltage enhancing section 26 is outputted from the output terminal 15. Polarity of the voltage which is enhanced in the CH2 output voltage enhancing section 27 is switched in a CH2 output polarity switching section 29 so as to form a similar low frequency pulse. Consequently, voltage which is enhanced in the CH2 output voltage enhancing section 27 is outputted from the output terminal 16. Here, the CH1 output polarity switching section 28 and the CH2 output polarity switching section 29 are controlled by the CPU 21.

A memory 22 which is formed by an EEPROM and the liquid crystal display section 14 are connected to the CPU 21. Furthermore, the switches 1 to 9 which are formed by twelve push-buttons and a reset section 30 which performs a power on resetting operation are connected to the CPU 21. Furthermore, a source oscillation device 31 which generates a dock is connected the CPU 21. Also, a power supply voltage monitoring section 32 in the CPU 21 monitors the power supply voltage Vcc. Here, memories such as a controlling program ROM and working RAM are formed in one-chip condition together with the CPU 21.

Consequently, operations in the above structure is explained.

The low frequency medical device in the present embodiment is operated under various modes such as a standard mode, a parameter protection mode, a parameter setting mode, or display mode for the quntity and the time for the medical operation selectively. Next, above modes are explained generally.

First, a standard mode is explained.

When a power is turned on from a power supply switch SW9, a standard mode is established. Either one of the modes such as a CONST mode, a BURST mode, a SURGE mode, a SWEEP mode, or a RANDOM mode is selected by the output mode selecting switch SW5. Next, outputs such as a level and intensity of the CH1 and CH2 are adjusted by the CH1 up-down switch SW1 and the CH2 output up-down switch SW2. Here, it is possible to adjust the output by every 1 (one) V as long as the voltage is between 0 to 45 V. The output of the low frequency pulse is started from 1V. Also, a timer starts counting the time synchronously with the start of the output such that the output is turned off after a time which is pre-set by a timer for the medical operation passes.

Also, when a key-lock switch SW6 is pushed down, the operations except the key-lock switch SW6 and the power supply switch SW9 are invalid. When the key-lock switch SW6 is pushed again, such a key-lock condition is released. The key-lock switch SW6 is valid only when the standard mode is established. Also, if the alternating switch SW7 is pushed when the SURGE mode is established, the outputs from the CH1 and the CH2 are performed alternately. If the alternating switch SW7 is pushed again, such alternate output stops.

Also, values which are stored in the memory 22 start being rewritten to be a default value by pushing the key-lock switch SW6, the alternating switch SW7, and the switch SW8 for displaying quantity and time for the medical operation simultaneously. During such a period, the liquid display blinks so as to be reset after the rewriting operation is completed.

Next, when the output is 0 (zero) in the above standard mode, if the parameter selecting switch SW4 and the output mode selecting switch SW5 are pushed simultaneously, the mode transcends to a parameter protection mode is established. First, the output mode is selected by the output mode selecting switch SW5 in the parameter protection mode. If either one of mode among a CONST mode, a BURST mode, a SURGE mode, or a SWEEP mode is selected except a RANDOM mode, an output frequency is set by the parameter setting up-down switch SW3 at first. Next, the output pulse width is set by the parameter setting up-down switch SW3. Furthermore, a time for the medical operation is set by the parameter setting up-down switch SW3 in a timer. Finally, the channel output is adjusted by the CH1 up-down switch SW1 and the CH2 output up-down switch SW2.

Here, it may be acceptable if the output is adjusted under condition that an electrode 17 is disposed on a human body of the user such that the output is set while the user realizes the output physically.

Also, in the RANDOM mode, the output is adjusted by the CH1 up-down switch SW1 and the CH2 output up-down switch SW2 after only the time for the medical operation is set by the parameter setting up-down switch SW3.

After the above setting operations are confirmed by pushing the parameter selecting switch SW4. The values for the confirmed parameters are stored in the memory 22 which is shown in FIG. 2.

Here, in the parameter protection mode, the medical operation is completed for 15 (fifteen) minutes in maximum with regardless to the settings in the timer. Also, the parameter protection mode is released if the parameter selecting switch SW4 and the output mode selecting switch SW6 are pushed simultaneously. Also, the parameter values are not stored while the parameters are being set. When the parameter protection mode is released, the parameter values are stored in the memory 22. Also, if the power supply is turned off during the medical operation, the latest parameter values before the power supply is turned off are stored.

Next, when the output is 0 (zero) in the standard mode, if the parameter selecting switch SW4 is pushed, the mode is transcends to a parameter setting mode. As similar to the above explained parameter protection mode, the output mode is selected and a frequency, a pulse width, a time for the medical operation are set and confirmed. The confirmed parameter values are stored in the memory. The parameter setting mode is performed in the same manner as that in the parameter protection mode except that the output is 0(zero) in the parameter setting mode.

Next, when the output is 0 (zero) in the standard mode, if the switch SW8 for displaying the quantity and the time for the medical operation is pushed, the mode transcends to a quantity and time for the medical operation display mode. In this mode, at first, an accumulative quantity for the medical operation is displayed. If the switch SW8 for displaying the quantity and the time for the medical operation is pushed again, an accumulative time for the medical operation so far is displayed. If the switch SW8 for displaying the quantity and the time for the medical operation is pushed furthermore under condition that the time for medical operation is displayed, the display blinks. If the switch SW8 for displaying the quantity and the time for the medical operation is pushed once more, the data for the quantity and the time for the medical operation are cleared; thus, the mode returns to the standard mode.

The quantity of medical operation and the time for the medical operation are measured during the medical operation such that accumulated value for the quantity and the time for the medical operation are stored in the memory 22 every time the medical operation is completed.

In the present embodiment, the above quantity and the time for the medical operation (data which include the quantity and the time in the latest 5 (five) minumtes) are loaded in the memory 22 after a predetermined period of time such as a five minutes passes after the user starts the medical operation. That is, if the user stops the medical operation by turning off the power supply within five minutes after the user starts the medical operation, the quantity and the time for the medical operation during such a period are not accumulated in the memory; thus, the physical therapist or the doctor may be able to know accurate values by checking the contents in the memory even if the user reports to the physical therapist or the doctor falsely.

Figure 3:
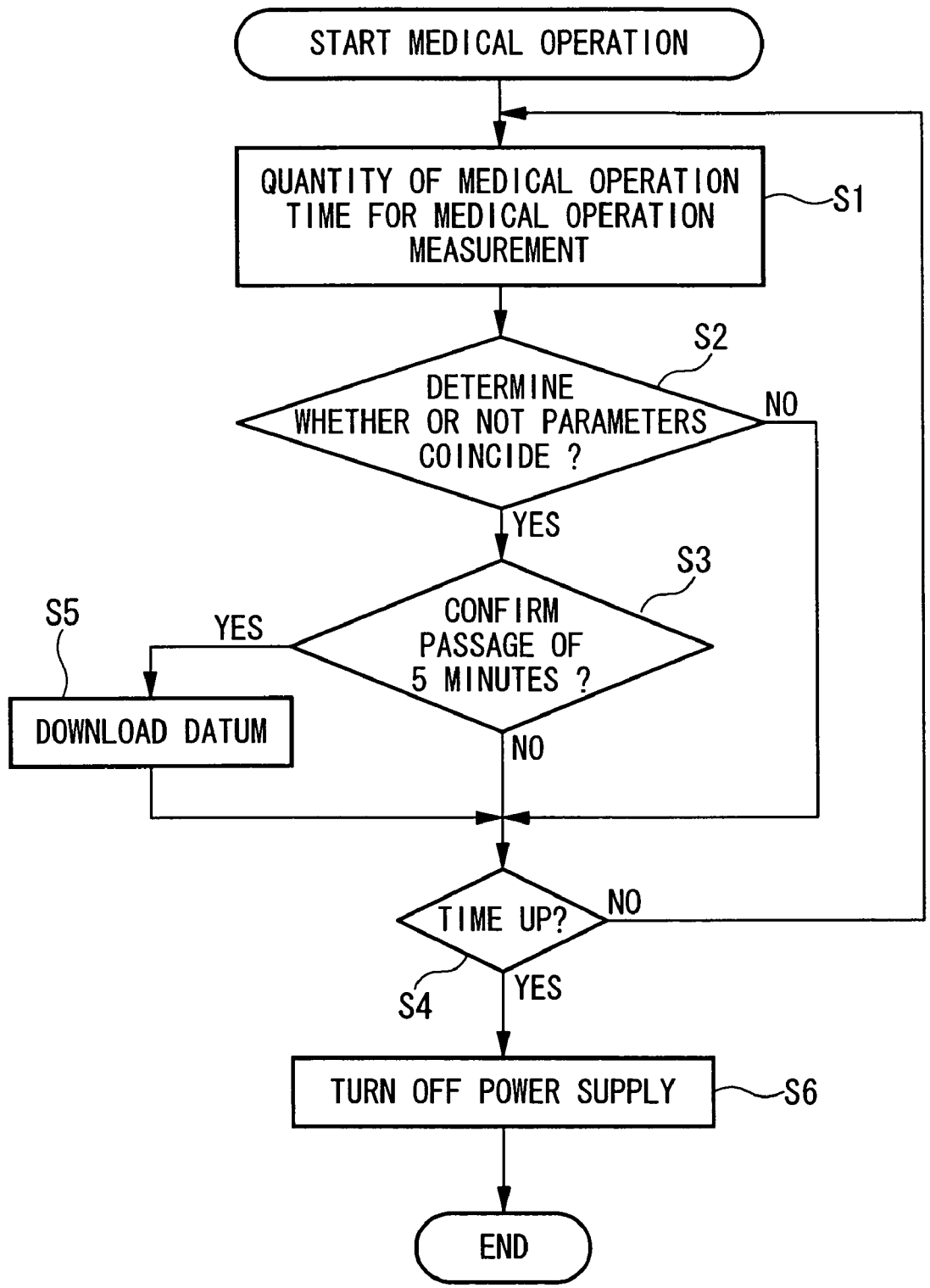
FIG. 3 is a flow chart of operations in the first embodiment of the low frequency medical device.

FIG. 3 is a flow chart for performing the above operations.

In FIG. 3, when the medical operation starts, the quantity and the time for the medical operation are measured (Step S1). Next, it is determined whether or not the parameter memories which are set by the physical therapist or the doctor and the parameters in the standard mode memory coincide (Step S2). If the parameters coincide, it is determined whether or not five minutes passes (Step S3). If the parameters do not coincide, it is determined whether or not the time expires after a predetermined period of time passes (Step S4). If it is determined that the time expires, the steps are completed because the power supply is turned off automatically (Step S6) by operating the switch manually or leaving the condition for a certain period of time. If it is determined that the time does not expire, the steps return to the step S1 so as to determine whether or not the power supply is turned off within five minutes in the step S3 while maintaining the measurement for the quantity and the time for the medical operation. After five minutes passes without turning off the power supply, the data which indicate the measurement result for the quantity and the time for the medical operation are loaded in the memory 22 (Step S5). After that, the latter operations after the time expires in the step S4 are performed.

According to the present embodiment, the data for the quantity and the time for the medical operation are loaded in the memory if a predetermined period of time passes after the medical operation starts and the parameter memories which are set by the physical therapist or the doctor and the parameters in the standard mode memory coincide. The physical therapist or the doctor may be able to know the quantity and the time for the medical operation in the low frequency medical device which is used by the user accurately so as to set the parameters for the next medical operation.

Also, if the user turns on and off the power supply so frequently or changes the parameters so variously that the condition for the medical operation is not constant in the above predetermined period of time, such a variance is acknowledged as a noise so as to be ignored. Therefore, it is possible to measure the quantity and the time for the medical operation reliably.

Also, the parameters which are confirmed and the latest parameters which are confirmed before the power supply is turned off are stored. Therefore, it is possible to know the parameter values which are confirmed by displaying these parameters and re-use these parameters.

Here, in the present embodiment, explanations are made for a case in which the quantity and the time for the medical operation are loaded in the memory. However, more importantly, it may be acceptable if the output electricity, the consumed electricity, the consumed wattage, etc. can be loaded in the memory.

Also, in the present embodiment, the parameters are loaded in the memory after a predetermined period of time passes. However, more importantly, it may be acceptable if the output electricity, the consumed electricity, or the consumed wattage, etc. reaches to the predetermined values. Also, if the patient changes the parameters which are set by the physical therapist or the doctor so as to perform the medical operation, such a period of time is not regarded as a medical operation from a view point of confirming whether or not the medical operation which is prescribed by the physical therapist or the doctor is performed reliably. That is, only when the parameters in the standard mode and the parameters in the parameter protection mode coincide when the medical operation starts or after the medical operation starts, the time for the medical operation is counted under condition that the medical operation is maintained and a predetermined period of time passes. If these parameters do not coincide, it is determined that the patient changes the parameters which are set by the physical therapist or the doctor; thus, the time for the medical operation is not counted.

Also, it is possible to determine whether or not the parameters in the standard mode and the parameters in the parameter protection mode coincide as similarly to the above case before starting the medical operation. If such a coincidence is established, time count is effective after a certain period of time passes by maintaining the medical operation under such a condition.

Figure 4:
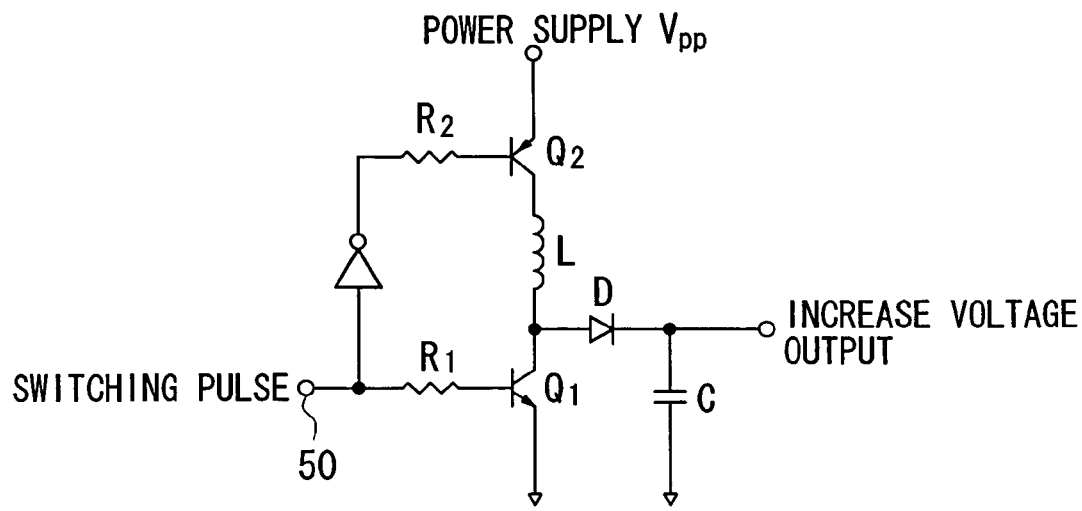
FIG. 4 is a circuit diagram for a pulse generating circuit in the low frequency medical device according to a second embodiment of the present invention.

FIG. 4 shows a general structure for an important portion in the pulse generating circuit in the low frequency medical device according to a second embodiment of the present invention. In FIG. 4, the same reference numerals are applied to corresponding members as shown in FIG. 5A so as to omit the repeated explanation thereof.

In the present embodiment, a PNP transistor Q2 is connected to an NPN transistor Q1 in serial as shown in the drawing such that a switching pulse for activating the transistor Q1 can be supplied to the transistor Q2 via an inverter IN and a resistance R2. Also, a pulse which has 31 kHz is used for a switching pulse. In a conventional case, such a pulse has approximately 10 kHz for the switching pulse.

According to the present embodiment, the transistors Q1 and Q2 are turned on and off synchronously by a common switching pulse such that the power supply voltage Vpp is shut down when the transistors are under OFF condition. Therefore, fewer electricity flows in the condenser C from the power supply; thus, it is possible to set a terminal voltage in the condenser C to be the power supply voltage such as 12V or lower. Also, the frequency for the switching operation is set at a high value; therefore, a resolution of the output voltage is high accordingly. For example, it is possible to adjust the output voltage by every 1V.

Next, a computer program and a recording medium for storing the computer program according to the present embodiment are explained.

A computer program for a CPU in a computer system in a device according to the present invention to perform operations according to the movements in FIG. 1 and processes shown in a flow chart in FIG. 3 forms a program for the present invention.

Also, a recording medium for storing the computer program forms a computer-readable recording medium according to the present invention. It is possible to use media such as an optical-magnetic disk, an optical disk, a semiconductor memory, and a magnetic recording medium for such a recording medium. These recording media may be used with a ROM (read-only-memory), a RAM (random-access-memory), a flexible disk, or a memory card.

Such a recording medium includes a volatile memory for maintaining a computer program for a certain period of time such as a RAM in a computer system which serves as a server or a client such that a program is transmitted via a network such as Internet or via a communication line such as a telephone line.

Also, it may be acceptable if the above computer program may be transmitted to other computer system from a computer system in which the above computer program is stored in a storage device etc. via a transmission medium or via a transmission wave in a transmission medium. Here, the above transmission medium indicates a medium which has a function for transmitting information. For example, it is possible to name a network (communication network) such as Internet and a communication circuit (communication line) such as a telephone line.

Also, it may be acceptable if the above computer program is used for realizing a part of the above function. Furthermore, it may be acceptable if the above computer program is formed by combining a computer program which is already stored in the computer system so as to realize the above function. For such a program, it is possible to name a differential file (differential program).

Therefore, it is possible to realize similar function and effect to the function and the effect which are explained in the above embodiments by using the computer program and the recording medium according to the present invention in a system or a device which are different from those in the drawing and executing the computer program by the computer system or the computer in the device; thus, it is possible to achieve the objects of the present invention.

What is claimed is:

1. A low frequency medical device for performing a medical operation by applying a low frequency pulse voltage to predetermined sections of a human body via electrodes comprising:
   means for producing a low frequency pulse;
   a measuring device for measuring a quantity and/or a time for the chiropractic medical operation by outputting the low frequency pulse;
   a timer device for measuring a predetermined time with reference to a start of the chiropractic medical operation;
   a detecting device for detecting a shut-down of a power supply; and
   a storage device for storing a time and/or a quantity for the chiropractic medical operation which are measured by the measuring device after the predetermined time passes under condition that the power supply is not shut down such that the chiropractic medical operation is performed by using parameters which are set by an operator of the chiropractic medical operation.

2. A low frequency medical device according to claim 1 further comprising:
   a parameter setting device for setting various parameters for forming the low frequency pulse; and
   a parameter storing device for storing the parameters for forming the low frequency pulse.

3. A low frequency medical device according to claim 2 wherein the parameters are at least a level of the low frequency pulse, the frequency, a pulse width, and a time for the chiropractic medical operation.

4. A low frequency medical device according to claim 3 wherein the storage device stores at least the quantity of the medial operation, the time for the chiropractic medical operation, a consumed electricity, and a consumed wattage.

5. A low frequency medical device according to claim 4 wherein:
   a detecting device for detecting whether or not the consumed electricity or the consumed wattage reaches at the predetermined value after the medical operation starts is disposed instead of the timer device; and
   the storage device stores the quantity of the chiropractic medical operation and/or the time for the chiropractic medical operation after it is detected that the power supply is not shut down such that the chiropractic medical operation is performed by using parameters which are set by an operator of the chiropractic medical operation and the consumed electricity and the consumed wattage reach to the predetermined values.

6. A low frequency medical device according to claim 5 further comprising a display device for displaying a stored content in the storage device.

7. A low frequency medical device according to claim 1 wherein the quantity of the chiropractic medical operation is indicated by a number of sessions for the chiropractic medical operation.

8. A method for a low frequency medical operation by applying a low frequency pulse voltage to predetermined sections of a human body via electrodes comprising the steps for:
   measuring a quantity and/or a time for the chiropractic medical operation by outputting of the low frequency pulse;
   measuring a predetermined time with reference to a start of the chiropractic medical operation;
   detecting a shut-down of a power supply; and
   storing a time and/or a quantity for the chiropractic medical operation which are measured by the measuring device after the predetermined time passes under condition that the power supply is not shut down such that the chiropractic medical operation is performed by using parameters which are set by an operator of the chiropractic medical operation.

9. A method for a low frequency medical operation according to claim 8 further comprising:
   setting various parameters for forming the low frequency pulse; and
   storing the parameters for forming the low frequency pulse.

10. A computer program product stored on a computer-readable medium including executable instructions that when executed by a professor performs steps for performing a medical operation by applying a low frequency pulse voltage to predetermined external sections of a human body via electrodes said steps comprising:
    measuring a quantity and/or a time for a chiropractic medical operation during outputting of the low frequency pulse;
    measuring a predetermined time with reference to a start of the chiropractic medical operation; detecting a shut-down of a power supply; and
    storing a time and/or a quantity for the chiropractic medical operation which are measured by the measuring device after the predetermined time passes under condition that the power supply is not shut down such that the chiropractic medical operation is performed by using parameters which are set by an physical therapist or a doctor.

11. A computer program according to claim 10 said steps further comprising:
    setting various parameters for forming the low frequency pulse; and
    storing the parameters for forming the low frequency pulse.

* * * * *